US00PP30793P2

(12) United States Plant Patent
Ashton

(10) Patent No.: US PP30,793 P2
(45) Date of Patent: Aug. 13, 2019

(54) ***DEUTZIA* PLANT NAMED 'LOW 18'**

(50) Latin Name: ***Deutzia* hybrid**
Varietal Denomination: Low 18

(71) Applicant: Ian J. Ashton, Warsash (GB)

(72) Inventor: Ian J. Ashton, Warsash (GB)

( * ) Notice: Subject to any disclaimer, the term of this patent is extended or adjusted under 35 U.S.C. 154(b) by 0 days.

(21) Appl. No.: 15/998,280

(22) Filed: Jul. 30, 2018

(51) Int. Cl.
*A01H 5/02* (2018.01)
*A01H 6/48* (2018.01)

(52) U.S. Cl.
USPC ..... Plt./226
CPC ..... *A01H 6/48* (2018.05); *A01H 5/02* (2013.01)

(58) Field of Classification Search
USPC ..... Plt./226
CPC ..... A01H 6/48; A01H 5/02
See application file for complete search history.

*Primary Examiner* — Kent L Bell
(74) *Attorney, Agent, or Firm* — Penny J. Aguirre

(57) ABSTRACT

A new cultivar of *Deutzia* plant named 'Low 18' that is characterized by its flowers that bloom along the entire branch, its flowers that are bright pink-purple in color with white centers and margins, its flowers that are large in size, and its freely branched and compact plant habit that is low maintenance.

2 Drawing Sheets

Botanical classification: *Deutzia* hybrid.
Varietal denomination: 'Low 18'.

CROSS REFERENCE TO A RELATED APPLICATION

This application is related to a European plant breeders' rights application filed on Jan. 9, 2016, application No. 2016/2114. There have been no offers for sale anywhere in the world prior to the effective filing date of this Application and no accessibility to one of ordinary skill in the art could have been derived from the printed plant breeder's rights documents.

STATEMENT DESIGNATING A GRACE PERIOD UNDER 102(b)(1)

The Applicant claims prior art exemption under 35 U.S.C. 102(b)(1) for disclosure and/or sales prior to the filing date but less than one year prior to the effective filing date if need be. Information about the claimed plant was obtained from a direct or indirect disclosure from the Inventors.

BACKGROUND OF THE INVENTION

The present invention relates to a new and distinct cultivar of *Deutzia* hybrid and will be referred to hereafter by its cultivar name, 'Low 18'. 'Low 18' represents a new *Deutzia*, a perennial shrub grown for landscape use.

'Low 18' arose from a cross made by the Inventor in June of 2011 in Warsash, Hampshire, United Kingdom between *Deutzia* 'Magicien' (not patented) as the female parent and an unnamed plant of *Deutzia setchuenensis* var *corymbifolia* as the male parent. The Inventor selected 'Low 18' as a single unique plant amongst the seedlings that resulted from the above cross in 2014.

Asexual propagation of the new cultivar was first accomplished by stem cuttings by the Inventor in Warsash, Hampshire, United Kingdom in 2014. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Low 18' as a unique cultivar of *Deutzia*.

1. 'Low 18' exhibits flowers that bloom along the entire branch.
2. 'Low 18' exhibits flowers that are bright pink-purple in color with white centers and margins.
3. 'Low 18' exhibits flowers that are large in size.
4. 'Low 18' exhibits a freely branched and compact plant habit that is low maintenance.

The female parent of 'Low 18' differs from 'Low 18' in having flowers that are less purple in color, a different flower cluster shape on young plants, leaves that are larger in size and a less compact plant habit. The male parent differs from 'Low 18' in having white flowers and a less compact plant habit. 'Low 18' can be most closely compared to the *Deutzia* cultivar 'Perle Rose' (not patented). 'Perle Rose' differs from 'Low 18' in having flowers that are a softer pink and less purple in color.

BRIEF DESCRIPTION OF THE DRAWINGS

The accompanying colored photographs illustrate the overall appearance and distinct characteristics of the new *Deutzia*. The photographs were taken of a plant 3.5 years in age as grown outdoors in a 23-cm container in Boskoop, The Netherlands.

The photograph in FIG. 1 provides a side view of the plant habit of 'Low 18' in bloom.

Figure 1:
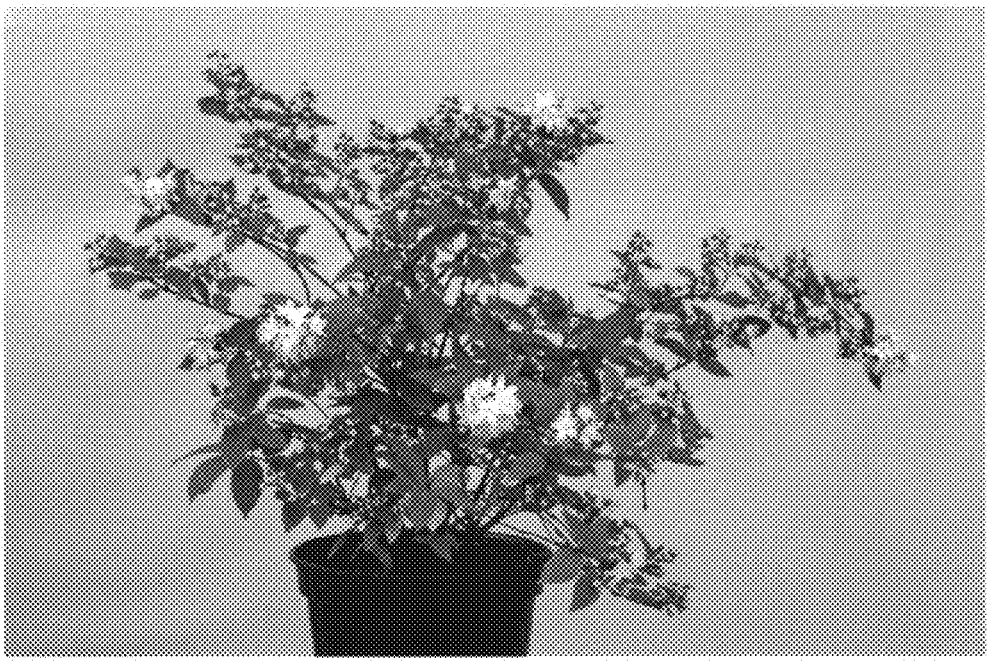
Figure 2:
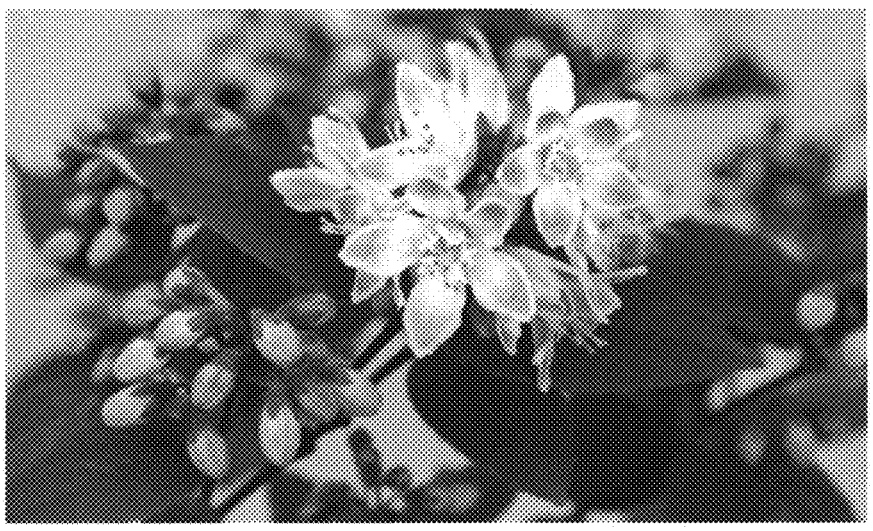

The photograph in FIG. 2 provides a close-up view of an inflorescence of 'Low 18'.

Figure 3:
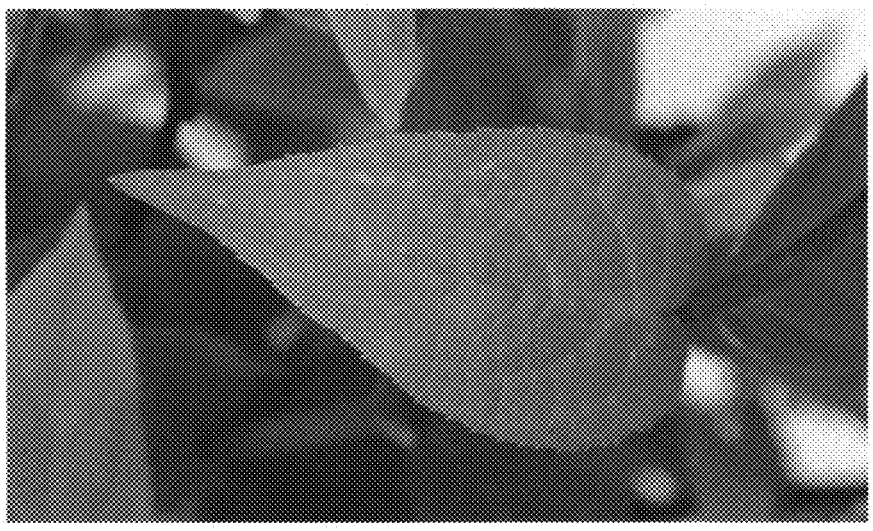

The photograph in FIG. 3 provides a close-up view of a leaf of 'Low 18'.

The colors in the photographs are as close as possible with the photographic and printing technology utilized and the color values cited in the detailed botanical description accurately describe the colors of the new *Deutzia*.

BOTANICAL DESCRIPTION OF THE PLANT

The following is a detailed description of plants 3.5 years in age as grown outdoors in 23-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Early summer in The United Kingdom.

*Plant type*.—Perennial shrub.

*Plant habit*.—Compact, upright and spreading.

*Height and spread*.—Up to 46.5 cm in height and 73.9 cm in spread as grown in a 23-cm container, reaches 1.5 m in height and 2 to 2.5 m in spread as a 5 year-old plant in the landscape.

*Hardiness*.—At least in U.S.D.A. Zones 5 to 9.

*Diseases and pests*.—No susceptibility and resistance to pests and diseases has been observed.

*Root description*.—Fibrous and fine.

*Propagation*.—Stem cuttings.

*Time required for root development*.—An average of 8 to 12 weeks for root initiation with a young rooted plant produced in about a year in a P9 container.

*Growth rate*.—Moderate.

Stem description:

*Stem shape*.—Rounded.

*Stem strength*.—Moderately strong.

*Stem quantity*.—Average of 48.

*Stem color*.—Young upper side 174A to 174B, lower side 148C to 148D, older bark N199C to N199D and 200A to 200B.

*Stem size*.—An average of 22.8 cm in length and 2 mm in diameter.

*Stem surface*.—Moderately pubescent with very small stellate hairs; an average of 0.1 mm in length and too small to measure color.

*Branching*.—Freely branching.

*Internode length*.—An average of 2.9 cm.

Foliage description:

*Leaf shape*.—Ovate to narrowly ovate.

*Leaf arrangement*.—Opposite.

*Leaf division*.—Simple.

*Leaf number*.—An average of 16 (8 pairs) per lateral branch.

*Leaf base*.—Obtuse to truncate.

*Leaf apex*.—Acuminate.

*Leaf margins*.—Finely serrate.

*Leaf venation*.—Pinnate, color; upper surface 144A, lower surface; 147D.

*Leaf size*.—An average of 5.5 cm in length and 2.6 cm in width.

*Leaf attachment*.—Petiolate.

*Leaf surface*.—Both surfaces are matte and moderately rough to the touch, moderately pubescent with short strigose and stellate hairs, average of 0.1 mm in length, too small to measure color.

*Leaf color*.—Young leaves; upper surface between 143B and 144A, lower surface 138B to 138C, mature leaves; upper surface between 143B and 144A, lower surface between 143C and 146C.

*Petioles*.—Average of 3.5 mm in length and 1 mm in diameter, 144C in color, pubescent surface.

Inflorescence description:

*Inflorescence type*.—Terminal and axillary thyrses on short lateral branchlets.

*Lastingness of inflorescence*.—Average of 10 days, self cleaning.

*Inflorescence number*.—12 per lateral stem.

*Inflorescence size*.—An average of 6.3 cm in height and 5.1 cm in diameter.

*Flower number*.—An average of 19 per inflorescence.

*Flower fragrance*.—Faint.

*Flower aspect*.—Held in multiple directions.

*Flower size*.—Average of 2.5 cm in diameter, 1.5 cm in depth.

*Flower shape*.—Rotate, single.

*Flower buds*.—Average of 1 cm in length, 5 mm in diameter, elliptic in shape, 77C in color, base 147C in color.

*Peduncles*.—An average of 4.7 cm in length and 1 mm in diameter, held upright, axillary peduncles held more in a 50° angle to lateral branches, color; N199C very slightly glossy surface is sparsely covered with short adpressed hairs, glabrous surface, moderately strong.

*Pedicels*.—An average of 4 cm in length and 0.6 mm in diameter, held at an average angle of 30° to peduncle, 177C in color, moderately strong, very slightly glossy surface is sparsely covered with short adpressed hairs; an average of 0.5 mm in length and NN155D in color, glabrous surface.

*Petals*.—5, rotate, elliptic to obovate in shape, upper surface matte and glabrous, lower surface slightly glossy, glabrous, margins fused, bluntly acute apex, 1.6 cm in length, 8 mm in width, when opening and fully open upper surface 77A and 77B, margins 76D, lower half NN155D, when opening and fully open lower surface 77D, margins 76D to NN155D.

*Sepals*.—5, rotate, ovate in shape, both surfaces matte and densely pubescent with very short stellate hairs average of 0.1 mm in length, 157A in color, margins entire, acute apex, 5 mm in length, 2.5 mm in width, when opening and fully open upper surface 144A, when opening lower surface 147C, fully open lower surface 147C, tip 178A.

*Calyx*.—Rotate, 5 mm in length, 9 mm in diameter.

Reproductive organs:

*Gynoecium*.—Pistils 3, an average of 1.2 cm in length, stigma; club-shaped and 150B in color, style; 1.15 cm in length and 150D in color, ovary is 147B to 147C in color.

*Androecium*.—Stamens; 10, 1 mm in length, anthers; basifixed, double kidney shaped, 15A in color, filaments; flattened with one tooth on each side, two rows of 5, outer row an average of 8 mm in length, 1 mm in width, inner row an average of 6 mm in length, 3 mm in width, pollen; low in quantity, 156D in color.

*Fruit and seed*.—No seeds or fruit observed to date.

It is claimed:

1. A new and distinct cultivar of *Deutzia* plant named 'Low 18' substantially as herein illustrated and described.

* * * * *